United States Patent
Kohno et al.

(10) Patent No.: US 6,174,730 B1
(45) Date of Patent: Jan. 16, 2001

(54) REAGENT FOR EVALUATING A HEPATIC OPERATION

(75) Inventors: Tadashi Kohno, Kanegawa; Isaburo Hosoi, Saitama; Junko Ohshima; Asuka Ito, both of Kanagawa; Kunihiko Shibata, Chiba, all of (JP)

(73) Assignee: Tokyo Gas Company Limited, Tokyo (JP)

( * ) Notice: Under 35 U.S.C. 154(b), the term of this patent shall be extended for 0 days.

(21) Appl. No.: 09/151,940

(22) Filed: Sep. 11, 1998

(30) Foreign Application Priority Data

Sep. 11, 1997 (JP) .................................................. 9-246688
Dec. 25, 1997 (JP) .................................................. 9-357619
Aug. 6, 1998 (JP) ................................................. 10-222914

(51) Int. Cl.[7] ............................ G01N 33/68; A61B 5/20; A61B 5/091
(52) U.S. Cl. .............................. 436/86; 436/811; 436/34; 436/900; 600/532; 128/898
(58) Field of Search ................. 436/86, 34, 811, 436/900; 128/898; 600/532

(56) References Cited

U.S. PATENT DOCUMENTS

| | | | |
|---|---|---|---|
| 5,302,520 | * 4/1994 | Goux | 435/94 |
| 5,386,832 | * 2/1995 | Wagner et al. | 128/665 |
| 5,413,917 | * 5/1995 | Malloy et al. | 435/35 |
| 5,961,470 | * 10/1999 | Wagner et al. | 600/532 |
| 5,962,335 | * 10/1999 | Katzman | 436/181 |

FOREIGN PATENT DOCUMENTS

| | | | |
|---|---|---|---|
| WO9201937 | 2/1992 | (WO) | G01N/33/60 |
| WO9205270 | 4/1992 | (WO) | C12P/19/02 |

OTHER PUBLICATIONS

Derwent Abstract XP–002089103, 1992.

"Test for Alcoholic Cirrhosis by Conversion of [$^{14}$C]–or [$^{13}$C]Galactose To Expired $CO_2$," Walton W. Shreeve, M.D., et al., vol. 71, No. 1, Gastroenterology 71:96–101, 1976.

"In Vivo Oxidation of [$^{13}$C]Galactose in Patients with Galactose–1–Phosphate Uridyltrasferase Deficiency," Gerard T. Berry et al., Biochemical and Molecular Medicine 56, 158–165 (1995).

"Breath tests: concepts, applications and limitations," D. Rating et al., Eur J Pediatr (1997) 156 [Suppl 1]: S18.

"Tracer Kinetic Studies on a Methionine–Supplemented Soy–Based Infant Formula Using 1–13C–and 15N–Methionine as Tracers," Michael Radke et al., Journal of Pediatric Gastroenterology and Nutrition 21:2029–214 ©1995.

Burke P.A. et al., The American Journal of Surgery 1997; 1973:270–274.

Mion F. et al.: Life Sciences 1994; 54: 2093–2098.

Walton W. et al.: Gastroenterology 1976; 71:98–101.

* cited by examiner

*Primary Examiner*—Jill Warden
*Assistant Examiner*—LaToya I. Cross
(74) *Attorney, Agent, or Firm*—Davidson, Davidson & Kappel, LLC (57) ABSTRACT

The present invention relates to a reagent for evaluating a hepatic operation, comprising an aromatic amino acid, methionine, alanine, fructose or galactose labelled with $^{13}$C at least at one position. According to the present invention, there is provided a reagent for evaluating a hepatic operation, which imposes less physical burden on a subject, can give accurate test results immediately and can be used safely without side effects. The reagent of the invention is useful for measuring the accurate liver excision ratio, liver regeneration/increase ratio or liver weight of a subject after a hepatic operation. With the reagent of the invention, information which is useful for evaluating a hepatic operation and the degree of invasion by the operation and for diagnosis is provided.

9 Claims, 12 Drawing Sheets

Time Course of $\Delta^{13}C$ (‰) after Intravenous Administration of 1-$^{13}$C-Phenylalanine before and after Liver Excision A: Left lobe-excised rat #1
B: Middle & left lobes-excised rat #2
C: Middle, left & right lobes-excised rat #3

(Peak in Regenerated Liver/Pre-Excision Peak)

Total $^{13}CO_2$ Exhalation (A.U.)

REAGENT FOR EVALUATING A HEPATIC OPERATION

BACKGROUND OF THE INVENTION

1. Field of the Invention

The present invention relates to a reagent for evaluating a hepatic operation with which the actual liver excision ratio by the operation, the liver regeneration/increase ratio or the liver weight of a patient after the hepatic operation can be measured safely and simply.

2. Description of the Prior Art

In liver excision which is one of the representative treating methods for liver cancer, the liver excision ratio (i.e. the ratio by weight of the excised liver to the total liver before the excision) and the weight of the remaining liver are important as numerical values representing objectively the evaluation of the excision and the degree of invasion by the excision. Together with the results of the liver function test, these values provide useful information for prognosis.

In order to know the liver excision ratio and the weight of the remaining liver mentioned above, measurement by weighing is most accurate. However, it is practically impossible to weigh the remaining liver though it is possible to weigh the excised liver.

At present, in order to determine the scope of a liver to be excised, it is possible to measure the ratio of this planned scope of excision from a total liver CT slice using an area measuring instrument prior to a hepatic operation [Ogasawara et al., Jpn. J. Surg. 25:43 (1995); Okamoto et al., Surgery 95:586 (1984); Yamanaka et al., Hepatology 18:79 (1993)]. After the operation, however, the patient is in an invaded state being connected with a plurality of tubes for transfusion or the like, and thus CT will impose a great burden on the patient. Besides, CT requires a high cost. Therefore, it is not realistic to practice this method in a large number of patients.

Besides, the system to calculate a liver volume from a total liver CT slice has spread little since the system is useful only for that purpose and very expensive. Furthermore, in the use of that system, a contrast medium is often administered to a patient to trace a liver slice from a CT image with a high sensitivity, which may cause the patient a shock.

On the other hand, the liver is an organ with a vigorous ability to regenerate. It regenerates and increases rapidly if the postoperative course is good after a liver excision or a liver transplantation operation, or a hepatic operation for various therapies such as embolization therapy, alcohol injection treatment and microwave coagulation therapy. Thus, it is thought that information concerning the liver regeneration/increase ratio and the liver weight after the regeneration is useful for judging unfavorable postoperative course and for managing treatment and nutrition [Hymsfield et al., Ann. Int. Med. 90:185 (1979)].

At present, what is commonly used as a parameter for the prognosis of a hepatic operation is a test method generically named the "liver function test", in which the ability to synthesize proteins such as serum albumin, the amounts of enzymes leaking from the liver, and the ability to include/excrete organic substances and drugs are measured (Merck Manual 16th Edition (1992)]. As one of the liver function test, there is the sugar tolerance test in which fructose or galactose is loaded to a subject and the ratio of its removal from the blood and the ratio of its retention in the blood are measured. However, these test results do not necessarily correlate with the liver regeneration/increase ratio.

Although determination by weighing is the most accurate way to know the liver regeneration/increase ratio and the liver weight of a patient, it is actually impossible to weigh the liver of a patient after a hepatic operation. To date, scintigraphy using 198Au or 99mTc [MacDermott and Weber, Surgery 54:56 (1963); Parker and Siemsen, Radiology 88:342 (1967); Barrett et al., Cancer 22:268 (1968); Aronsen et al., Ann. Surg. 171:567 (1970)] and the determination of a liver volume by CT [Hymsfield et al., Ann. Int. Med. 90:185 (1979); Yamanaka et al., Hepatology 18:79 (1993)]. However, these methods have various problems such as heavy physical burden imposed on patients, exposure to radiation and a very high price of the system.

The liver is a major organ which metabolizes aromatic amino acids; in particular, phenylalanine and tyrosine are metabolized in the liver for the most part [Essential of Human Metabolism, W. C. McMurray Harper & Row Publishers, N.Y., (1983)]. A liver function test method noting this point has been reported recently. This method comprises administering $^{13}C$-labelled phenylalanine to a subject, measuring $^{13}CO_2$ discharged into the exhalation and evaluating the phenylalanine metabolizing ability of the liver from the degrees of increase of the $^{13}CO_2$ [U.S. Pat. No. 5,386,832; Burke et: al., Am J. Surgery 173:270 (1997)]. However, correlation with liver regeneration/increase ratios has not been examined at all.

Since the liver is also a major metabolic organ for methionine, alanine and galactose [Essential of Human Metabolism, W. C. McMurray Harper & Row Publishers, N.Y., (1983)], methods for evaluating liver functions by administering to a subject $^{13}C$-labelled methionine or alanine [Japanese Patent No. 2680861] or $^{13}C$-labelled galactose [Mion F. et al., Life Sciences 54:2093 (1994); Walton W. et al., Gastroenterology 71:98 (1976)] and measuring the degrees of increase of $^{13}CO_2$ discharged into the exhalation have been reported. However, correlation with liver regeneration/increase ratios has not been examined at all in these methods.

As described above, although the liver excision ratio, the liver regeneration/increase ratio or the liver weight of a patient after a hepatic operation is important for evaluating the operation, there has been no effective means to obtain such information. Thus, almost nothing is done to obtain such information at present.

Under circumstances, it is desired to provide a means to measure safely and simply the liver excision ratio, the liver regeneration/increase ratio or the liver weight of a patient after a hepatic operation which would be an important parameter for evaluating the operation.

OBJECTS AND SUMMARY OF THE INVENTION

It is an object of the present invention to provide a reagent for evaluating a hepatic operation, with which the liver excision ratio, the liver regeneration/increase ratio or the liver weight of a patient after the hepatic operation can be measured safely and simply regardless of the conditions of the patient.

Toward the solution of this problem, the present inventors have made intensive and extensive researches. As a result, the inventors have found that it is possible to accurately measure the liver excision ratio, the liver regeneration/increase ratio or the liver weight of a patient after a hepatic operation by administering to the patient once or a plurality of times an aromatic amino acid, methionine, alanine, fructose or galactose labelled with $^{13}C$ and measuring degrees of increase of $^{13}C$ level in the exhaled $CO_2$. Thus, the present invention has been achieved.

The present invention relates to a reagent for evaluating a hepatic operation, comprising an aromatic amino acid, methionine, alanine, fructose or galactose labelled with $^{13}C$ at least at one position.

DETAILED DESCRIPTION OF THE INVENTION

Hereinbelow, the present invention will be described in detail.

The aromatic amino acid, methionine, alanine fructose or galactose in the present reagent for evaluating a hepatic operation is an aromatic amino acid, methionine, alanine fructose or galactose labelled with $^{13}C$ at least at one position. The position of labelling is not particularly limited. Preferable aromatic amino acids include, but are not limited to, phenylalanine and tyrosine.

Because $^{13}C$ is a stable isotope, there is no danger of exposure to radiation which might be caused by a radioactive isotope. Thus, there is no problem in the safety of the reagent of the invention.

The evaluation of the liver excision ratio, the liver regeneration/increase ratio or the liver weight of a patient using the reagent of the invention is performed by administering the reagent one time or continuously to the patient immediately before the operation, or after the operation and after a specific period, and subsequently measuring degrees of increase of $^{13}C$ levels in the exhaled $CO_2$. More specifically, degrees of increase of $^{13}C$ levels in the exhaled $CO_2$ ($\Delta^{13}C$ (‰)) at predetermined intervals (e.g. 5 min, 10 min, 15 min) after administration of the reagent; total amount of $^{13}CO_2$ exhalation for a predetermined time after administration of the reagent; and the time course (peak value, slope at the start, change in the slope, peak time, etc.) of degrees of increase of $^{13}C$ levels in the exhaled $CO_2$ ($\Delta^{13}C$ (‰)) for a predetermined time after administration of the reagent are measured, followed by calculation of ratios before and after the operation to evaluate the ratio or weight of interest.

$^{13}C$ levels in exhaled $CO_2$ can be determined using gas chromatography mass spectrometry (GC-MS), infrared spectrophotometry, mass spectrometry, photoelectric acoustic spectrophotometry and NMR (nuclear magnetic resonance).

The reagent of the invention for evaluating a hepatic operation can be formulated into pharmaceutical preparations such as parenteral agents (tablets, capsules, powder, granules, liquid, etc.), injections and the like, depending on the administration route, by using the above-described aromatic amino acid, methionine, alanine (hereinafter, referred to as the "labelled amino acid"), fructose or galactose (hereinafter, referred to as the "labelled saccharide") labelled with $^{13}C$ alone or mixing it with fillers or carriers. The fillers or carriers may be any of those conventionally used in this field as long as they are pharmaceutically acceptable. The type and composition of such pharmaceutical preparations are altered appropriately according to the route and method of administration. For example, water is used as a liquid carrier. As solid carriers, cellulose derivatives such as hydroxypropyl cellulose and organic acid salts such as magnesium stearate are used. Water, physiological saline and various buffer solutions are generally desirable in the preparation of injections. Such preparations may be lyophilized for use as oral medicines, or the lyophilized preparations may be dissolved in suitable injection solvents e.g. liquids for intravenous administration, such as sterilized water, physiological saline, electrolyte, etc. just before use.

The content of the labelled amino acid or saccharide in the pharmaceutical preparation varies according to the type of the preparation, and is usually in the range of 1 to 100% by weight, preferably 50 to 100% by weight. In the case of injections, for example, the labelled amino acid or saccharide is added usually in an amount of 1 to 40% by weight. In the case of capsules, tablets, granules and powder, the content of the labelled amino acid or saccharide is in the range from about 10 to 100% by weight, preferably 50 to 100% by weight, with the remainder being carriers.

The reagent of the invention for evaluating a hepatic operation should be administered at such a dosage that enables the confirmation of an increase of $^{13}C$ levels in an exhalation after administration. Depending on the age and weight of the patient and the object of breath test, the dosage for each administration ranges from 1 to 1000 mg/kg body weight in the case of an adult.

The reagent of the invention for evaluating a hepatic operation can be used for accurate evaluation of the liver excision ratio, the liver regeneration/increase ratio or the liver weight after a hepatic operation of a patient having a hepatic disease such as liver cancer. From these ratios or weight, information useful for evaluation of the hepatic operation, evaluation of the degree of invasion, and judgment of the postoperative conditions is provided.

EFFECT OF THE INVENTION

According to the present invention, there is provided a reagent for evaluating a hepatic operation which imposes less physical burden on a patient, can give accurate test results immediately, and can be used safely without side effects. The reagent of the invention is useful for measuring the accurate liver excision ratio, liver regeneration/increase ratio or liver weight of a patient after hepatic operation. From these ratios or weight, information useful for evaluation of the hepatic operation, evaluation of the degree of invasion, and judgment of the postoperative conditions is provided.

PREFERRED EMBODIMENTS OF THE INVENTION

Hereinbelow, the present invention will be described more specifically below with reference to the following Examples. However, the scope of the present invention is not limited to these Examples.

The $^{13}C$ purity at the position of labelling in the labelled phenylalanine, methionine, alanine, fructose and galactose used the following Examples is 99% or more. Unless otherwise indicated, all the reagents used were guaranteed reagents.

EXAMPLE 1

Determination of Liver Excision Ratio (by 1-$^{13}C$-Phenylalanine Breath Test)

I. Methods (1) Preparation of partially liver-excised rats

As test animals, male Wister rats were bred at 23±2° C. under 55±10% humidity before use. The rats (9 week-old) fasted overnight were anesthetized by intraperitoneal administration of Nembutal (50 mg/kg), and then the abdomen was opened. According to the method of Higgins and Anderson (Archives of Pathology 12, 183, 1931), the left lobe of the liver was excised in Group A (n=3), the middle and left lobes of the liver were excised in Group B (n=3), and the middle, left and right lobes of the liver were excised in Group C (n=4). Thus, 3 types of partially liver-excised rats were prepared.

(2) Measurement of $^{13}C$ levels in exhaled $CO_2$ $^{13}C$ levels in exhaled $CO_2$ were measured in the rats 2 days before the partial liver excision and immediately after the excision.

The rat anesthetized by intraperitoneal administration of Nembutal (50 mg/kg) was fixed on an operation table, and then covered its head with a cap for sucking its exhalation. 1-$^{13}C$-phenylalanine (purchased from CIL) dissolved in physiological saline was administered from the femoral vein (20 mg/kg). The exhalation was sucked with a stroke pump (variable stroke pump VS-500; Shibata Scientific Technology) at a rate of 100 ml/min and introduced into a flow cell in $^{13}CO_2$ Analyzer EX-130S (Japan Spectroscopic Co., Ltd.). A column packed with silica gel was located between the cap and the stroke pump to remove the moisture in the exhalation.

The data output from the $^{13}CO_2$ analyzer were incorporated into a personal computer (Apple Power Macintosh 8500) after AD conversion. Using the data processing software Lab VIEW (National Instruments), data on 10 points at every 100 msec were added up and averaged at intervals of 5 sec and then converted into $^{13}C$ atom %, $\Delta^{13}C$ (‰) and $CO_2$ gas concentration (%), to thereby perform a continuous measurement. The converted data were displayed on the screen in real time and then stored in the hard disk. During the measurement of $^{13}C$ levels in exhaled $CO_2$, the rectum temperature in the rat was monitored and maintained at 37±0.5° C. using a body temperature controller for small animals (TR-100; Fine Science Tools Inc.). The $CO_2$ gas concentration in the sucked exhalation was maintained at 3±0.5%.

[Calculation method for $\Delta^{13}C$ (‰)]

$\Delta^{13}C$ (‰) was calculated from the $^{13}C$ level in exhaled $CO_2$ at each time point ($^{13}C$ tmin) and the $^{13}C$ level in standard $CO_2$ gas ($^{13}C$ std) using the following formula:

$$\Delta^{13}C\ (‰)=[(^{13}C\ t\ min-^{13}C\ 0\ min)/^{13}C\ std]\times 1000$$

(3) Measurement of the liver excision ratio

After the partial liver excision, the excised liver was immediately weighed. Also, after completion of the measurement of post-excision $^{13}C$ levels in exhaled $CO_2$, the remaining liver was removed and weighed. From the weighing results, the liver excision ratio was calculated as follows:

Liver excision ratio (%)=[(Weight of excised liver)/(Weight of remaining liver+Weight of excised liver)]×100 (Weight in gram)

II. Results

Figure 1:
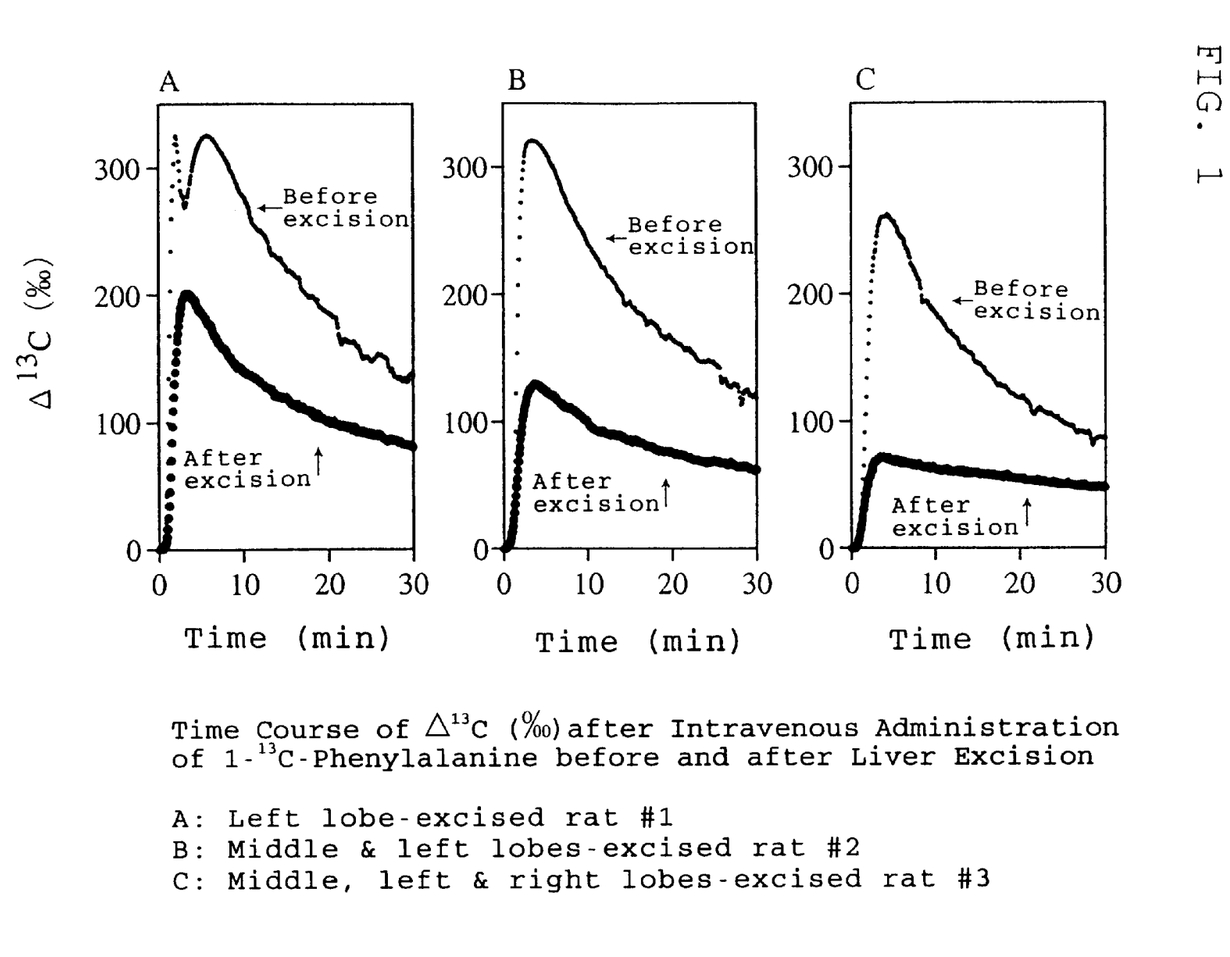
FIG. 1 shows degrees of increase of $^{13}C$ levels in exhaled $CO_2$ after administration of 1-$^{13}C$-phenylalanine in one rat from each group.

In the measurement of pre-excision $^{13}C$ levels in exhaled $CO_2$ after intravenous administration of 1-$^{13}C$-phenylalanine, the $\Delta^{13}C$ values (‰) sharply increased to respective peak values of 286.33±69. 57 ‰ in Group A, 324±1 ‰ in Group B, and 290.25+32.07 ‰ in Group C in about 2.5 min after the administration. Then, these values began to decrease. At 30 min after administration, the $\Delta^{13}C$ values (‰) decreased to about ½ of the peak values (FIG. 1).

In the measurement of post-excision $^{13}C$ levels in exhaled $CO_2$ after intravenous administration of 1-$^{13}C$-phenylalanine, the $\Delta^{13}C$ values (‰) were lower than those values before the liver excision in any of the liver-excised rats in Groups A to C. The $\Delta^{13}C$ peak values (‰) were 181.67±33.49 (‰) in Group A (n=3), 138.00±34.39 (‰) in Group B (n=3), and 63.00±23.64 (‰) in Group C (n=4). The more the liver was excised, the more the $\Delta^{13}C$ value (‰) after the excision decreased.

The degrees of decrease of $\Delta^{13}C$ values (‰) after the liver excision were evaluated using ratios of the post-excision $\Delta^{13}C$ peak value (‰) to the pre-excision $\Delta^{13}C$ peak value (‰). The peak ratios in the three groups were in the following order: Group A: left lobe-excised rats (n=3)>Group B: middle and left lobes-excised rats (n=3) >Group C: middle, left and right lobes-excised rats (n=4). The more the liver was excised, the more the peak ratio decreased (Table 1).

TABLE 1

Ratio (%) of the Post-Excision Δ¹ ³C Peak Value (‰)
to the Pre-Excision Δ¹ ³C Peak Value (‰)

| Rat # | Group A<br>Left Lobe<br>Excised | Group B<br>Middle & Left Lobes<br>Excised | Group C<br>Middle, Left & Right<br>Lobes Excised |
|---|---|---|---|
| #1 | 61.66% | 54.15% | 10.06% |
| #2 | 61.47% | 39.81% | 27.67% |
| #3 | 69.42% | 33.75% | 27.59% |
| #4 |  |  | 22.73% |

Table 2 shows the liver excision ratio calculated from the weight of the excised liver and the weight of the remaining liver after the partial liver excision.

TABLE 2

Liver Excision Ratio (%)

| Rat # | Group A<br>Left Lobe<br>Excised | Group B<br>Middle & Left Lobes<br>Excised | Group C<br>Middle, Left & Right<br>Lobes Excised |
|---|---|---|---|
| #1 | 31.69% | 67.11% | 88.25% |
| #2 | 31.97% | 71.29% | 72.13% |
| #3 | 31.00% | 65.14% | 75.07% |
| #4 |  |  | 80.16% |

Figure 2:
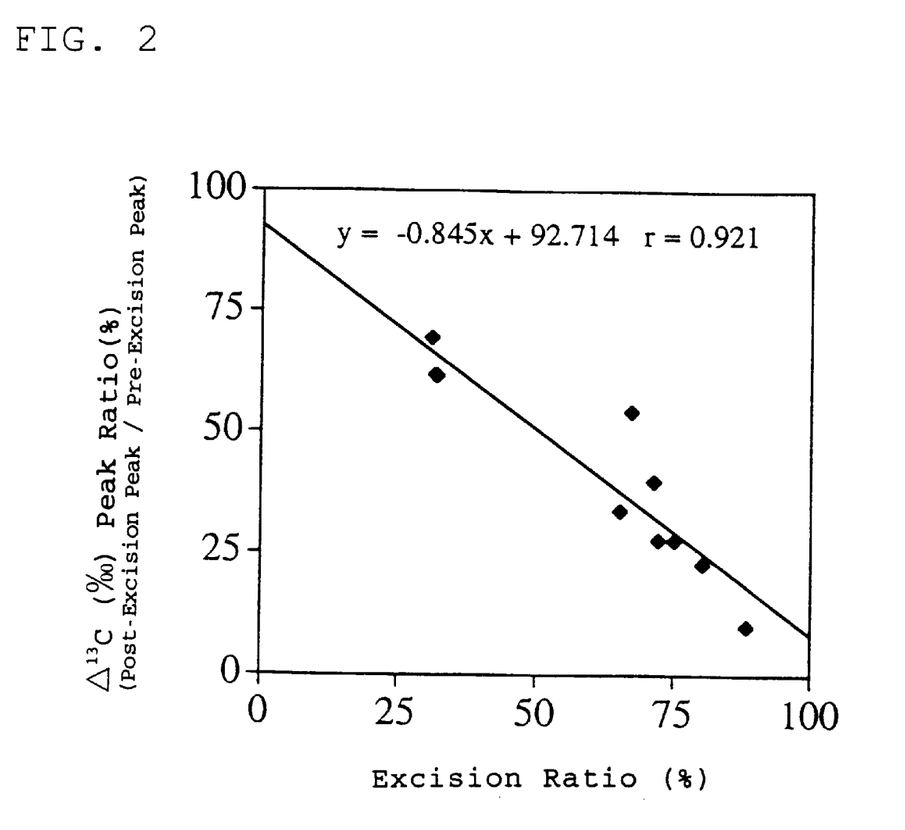
FIG. 2 shows correlation between liver excision ratios and ratios of the $\Delta^{13}C$ peak value (‰) after a liver excision to the $\Delta^{13}C$ peak value (‰) before the excision in 1-$^{13}C$-phenylalanine breath test.

When the liver excision ratio calculated from the weight of the excised liver and the weight of the remaining liver, and the ratio of the post-excision $\Delta^{13}C$ peak value (‰) to the pre-excision $\Delta^{13}C$ peak value (‰) were plotted, high correlation was observed (correlation factor=0.921). (FIG. 2)

Accordingly, by comparing the post-excision and pre-excision $\Delta^{13}C$ values (‰) at a specific time after administration of 1-$^{13}C$-Phenylalanine, or by comparing the post-excision $\Delta^{13}C$ peak value (‰) to the pre-excision $\Delta^{13}C$ peak value (‰) after administration of 1-$^{13}C$-Phenylalanine, the liver excision ratio can be evaluated.

EXAMPLE 2

Determination of Liver Regeneration Ratio (by 1-$^{13}C$-Phenylalanine Breath Test)

I. Methods (1) Preparation of partially liver-excised rats

As test animals, male Wister rats were bred at 23±2° C. under 55±10% humidity before use. The rats (9 week-old) fasted overnight were anesthetized by intraperitoneal administration of Nembutal (50 mg/kg), and then the abdomen was opened. According to the method of Higgins and Anderson (Archives of Pathology 12, 183, 1931), the middle and left lobes of the liver were excised and immediately weighed.

(2) Measurement of $^{13}C$ levels in exhaled $CO_2$

Immediately before the partial liver excision and after the excision (1, 3, 7 or 14 days after the excision), the rats were anesthetized by intraperitoneal administration of Nembutal (50 mg/kg) and fixed on an operation table. The head was covered with a cap for sucking the exhalation, which was sucked with a stroke pump (variable stroke pump VS-500; Shibata Scientific Technology) at a rate of 100 ml/min and introduced into a flow cell in $^{13}CO_2$ Analyzer EX-130S (Japan Spectroscopic Co., Ltd.). After the $CO_2$ gas concentration in the sucked exhalation was stabilized at about 3%, 1-$^{13}C$-phenylalanine (purchased from CIL) dissolved in physiological saline was administered from the femoral vein (20 mg/kg). A column packed with silica gel was located between the cap and the stroke pump to remove the moisture in the exhalation. During the measurement of $^{13}C$ levels in exhaled $CO_2$, the rectum temperature in the rat was monitored and maintained at 37±0.5° C. using a body temperature controller for small animals (TR-100; Fine Science Tools Inc.).

The data output from the $^{13}CO_2$ analyzer were incorporated into a personal computer (Apple Power Macintosh 8500) after AD conversion. Using the data processing software Lab VIEW (National Instruments), data on 10 points at every 100 msec were added up and averaged at intervals of 5 sec and then converted into $^{13}C$ atom %, $\Delta^{13}C$ (‰) and $CO_2$ gas concentration (%), to thereby perform a continuous measurement. The converted data were displayed on the screen in real time and then stored in the hard disk. $\Delta^{13}C$ (‰) was calculated by the formula described previously.

(3) Calculation of the liver regeneration ratio

After completion of the measurement of $^{13}C$ levels in exhaled $CO_2$ performed after the partial liver excision, the total liver, i.e. the regenerated liver was removed and immediately weighed.

In order to determine the excision ratios by the excision of the middle and left lobes of the liver in the rats used in this experiment, an experiment was conducted in advance in which a similar partial liver excision was performed; the remaining liver was removed immediately; and the excised liver and the remaining liver were weighed. As a result, the excision ratio was found to be 68.0±1.0% (n=6). Thus, liver regeneration can be calculated from the results of weighing of the excised liver and the regenerated liver using the following formula:

Liver regeneration ratio (%)=[(Weight of regenerated liver)/(Weight of excised liver/0.68)]×100 (Weight in gram)

II. Results

Liver regeneration after the partial liver excision gradually progressed from 40.7±3.8% (n=4) at day 1, to 57.7±5.8% (n=6) at day 3, and to 63.3±13.7% (n=4) at day 7 after the excision. The liver was regenerated up to 90.2±7.9% (n=4) at day 14 after the excision.

Figure 3:
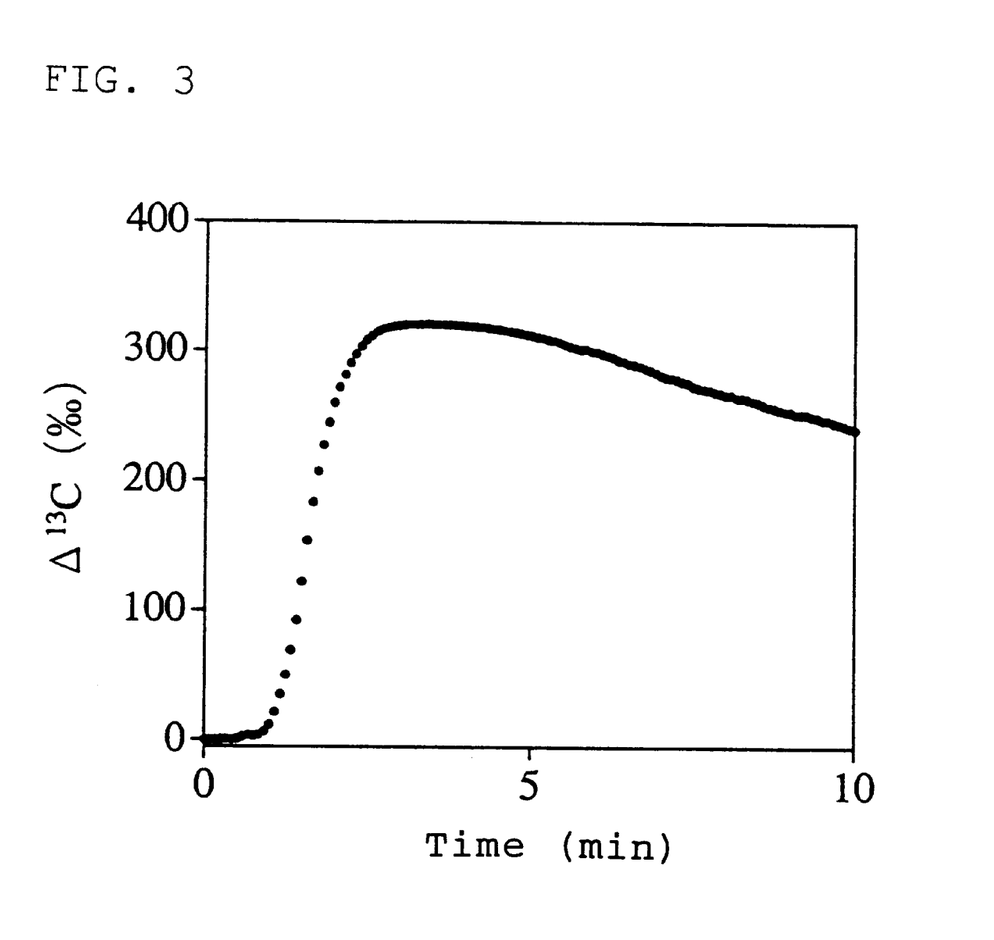
FIG. 3 shows one example of the time course of $^{13}C$ levels in exhaled $CO_2$ ($\Delta^{13}C$ (‰)) after administration of 1-$^{13}C$-phenylalanine performed immediately before a partial liver excision.
Figure 4:
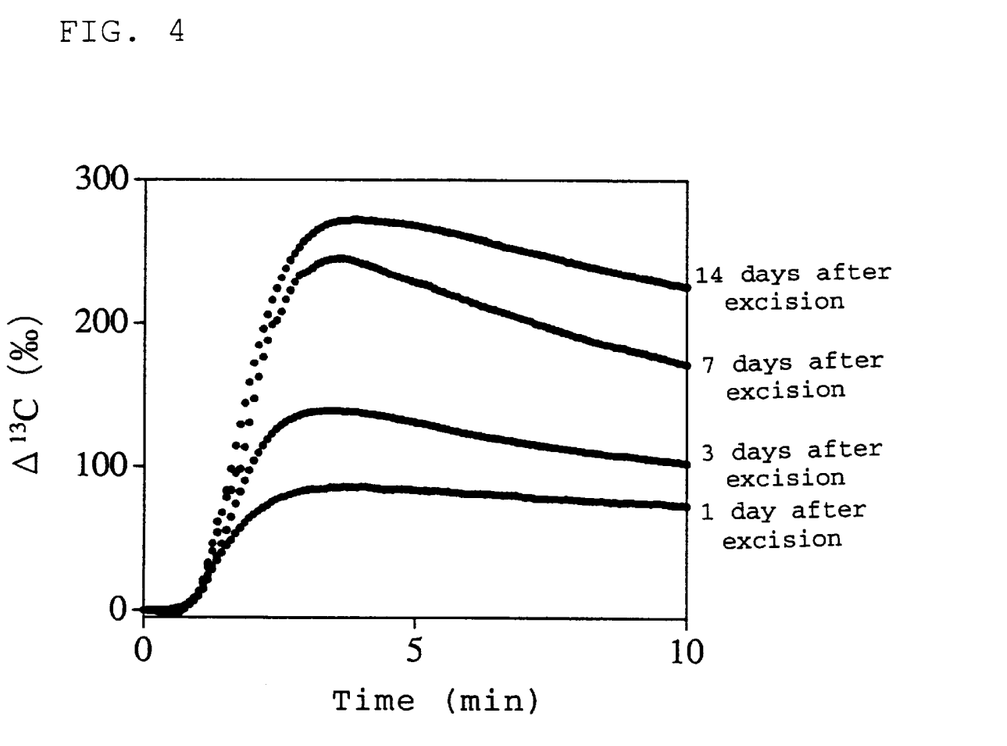
FIG. 4 shows one example each of the time course of $^{13}C$ levels in exhaled $CO_2$ ($\Delta^{13}C$ (‰)) after administration of 1-$^{13}C$-phenylalanine performed 1, 3, 7 or 14 days after a partial liver excision.

In the measurement of $^{13}C$ levels in exhaled $CO_2$ after intravenous administration of 1-$^{13}C$-phenylalanine performed immediately before the the liver excision, the $\Delta^{13}C$ value (‰) sharply increased after the administration, reached the peak in about 2.5 min (309.1±19.3 ‰ (n=18)) and then gradually decreased (FIG. 3). After the partial liver excision, the $\Delta^{13}C$ (‰) value exhibited the same pattern as seen before the excision in that the value increased sharply after administration of 1-$^{13}C$-phenylalanine and reached the peak in about 2.5 min. However, the peak value was remarkably lowered at day 1 after the partial liver excision (86.2±9.9 ‰ (n=4)). Thereafter, the peak value increased to 139.0±19.7 ‰ (n=6) at day 3 and to 245.4±45.5 ‰ (n=4) at day 7 after the excision, as the regeneration of the liver progressed. At day 14 after the excision, the peak value reached 272.6±15.2 ‰ (n=4) which is close to the value before the excision (FIG. 4).

Figure 5:
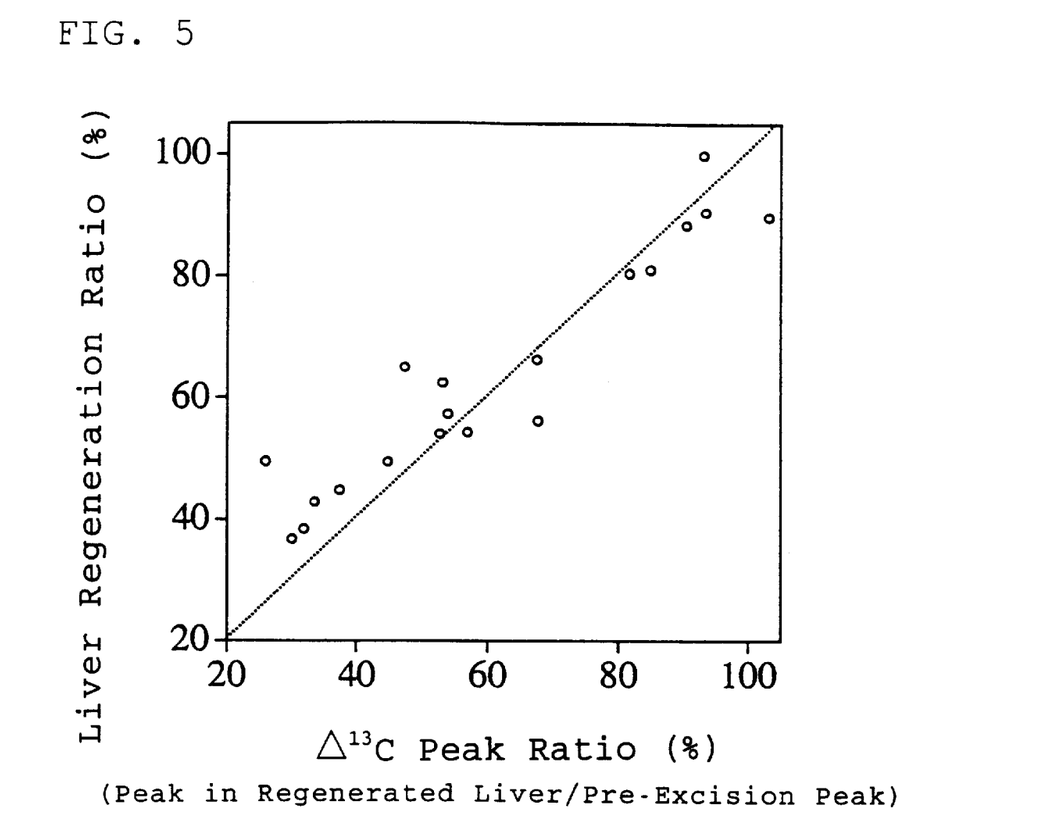
FIG. 5 shows correlation between individual liver regeneration ratios (%) and individual ratios of the $\Delta^{13}C$ peak value (‰) after the excision and breeding to the $\Delta^{13}C$ peak value (‰) before the excision, i.e. [post-excision/breeding $\Delta^{13}C$ peak value (‰)/pre-excision $\Delta^{13}C$ peak value (‰)]×100 (%) in 1-$^{13}C$-phenylalanine breath test.

When individual liver regeneration ratios (%) and the ratios of the pre-excision $\Delta^{13}C$ peak values (‰) to the post-liver excision $\Delta^{13}C$ peak value (‰), i.e. [post-excision/breeding $\Delta^{13}C$ peak value (‰)/pre-excision $\Delta^{13}C$ peak value (‰)]×100(%) in 1-$^{13}C$-phenylalanine breath test were plotted, high correlation [correlation factor: 0.904 (p<0.001)] was observed (FIG. 5).

Accordingly, by comparing the $\Delta^{13}C$ peak value (‰) before the excision with the $\Delta^{13}C$ peak value (‰) during the course of recovery after the excision, the liver regeneration ratio can be evaluated.

EXAMPLE 3

Determination of Liver Regeneration Ratio (by 1-$^{13}$C-Methionine Breath Test)

I. Methods (1) Preparation of partially liver-excised rats

As test animals, male Wister rats were bred at 23±2° C. under 55±10% humidity before use. The rats (12–15 week-old) fasted overnight were anesthetized by intraperitoneal administration of Nembutal (50 mg/kg), and then the abdomen was opened. According to the method of Higgins and Anderson (Archives of Pathology 12, 183, 1931), the middle and left lobes of the liver were excised and immediately weighed.

(2) Measurement of $^{13}$C levels in exhaled $CO_2$

Immediately before the partial liver excision and after the excision (1, 3, 7 or 14 days after the excision), the rats were anesthetized by intraperitoneal administration of Nembutal (50 mg/kg) and fixed on an operation table. The head was covered with a cap for sucking the exhalation, which was sucked with a stroke pump (variable stroke pump VS-500; Shibata Scientific Technology) at a rate of 100 ml/min and introduced into a flow cell in $^{13}CO_2$ Analyzer EX-130S (Japan Spectroscopic Co., Ltd.). After the $CO_2$ gas concentration in the sucked exhalation was stabilized at about 3%, 1-$^{13}$C-methionine (purchased from mass Trace) dissolved in physiological saline was administered from the femoral vein (40 mg/kg). A Perma Pure Drier (MD-050-12P; Perma Pure Inc.) was located between the cap and the stroke pump to remove the moisture in the exhalation. During the measurement of $^{13}$C levels in exhaled $CO_2$, the rectum temperature in the rat was monitored and maintained at 37±0.5° C. using a body temperature controller for small animals (TR-100; Fine Science Tools Inc.).

The data output from the $^{13}CO_2$ analyzer were incorporated into a personal computer (Apple Power Macintosh 8500) after AD conversion. Using the data processing software Lab VIEW (National Instruments), data on 10 points at every 100 msec were added up and averaged at intervals of 5 sec and then converted into $^{13}$C atom %, $\Delta^{13}$C (‰) and $CO_2$ gas concentration (%), to thereby perform a continuous measurement. The converted data were displayed on the screen in real time and then stored in the hard disk. $\Delta^{13}$C (‰) was calculated by the formula described previously.

(3) Calculation of the liver regeneration ratio

After completion of the measurement of $^{13}$C levels in exhaled $CO_2$ performed after the partial liver excision, the total liver, i.e. the regenerated liver was removed and immediately weighed. The liver regeneration ratio was calculated from the formula described previously.

II. Results

Liver regeneration after the partial liver excision gradually progressed from 42.0±2.6% (n=6) at day 1, to 48.1±3.6% (n=6) at: day 3, and to 73.2±10.6% (n=7) at day 7 after the excision. The liver was regenerated up to 96.1±12.7% (n=6) at day 14 after the excision.

Figure 6:
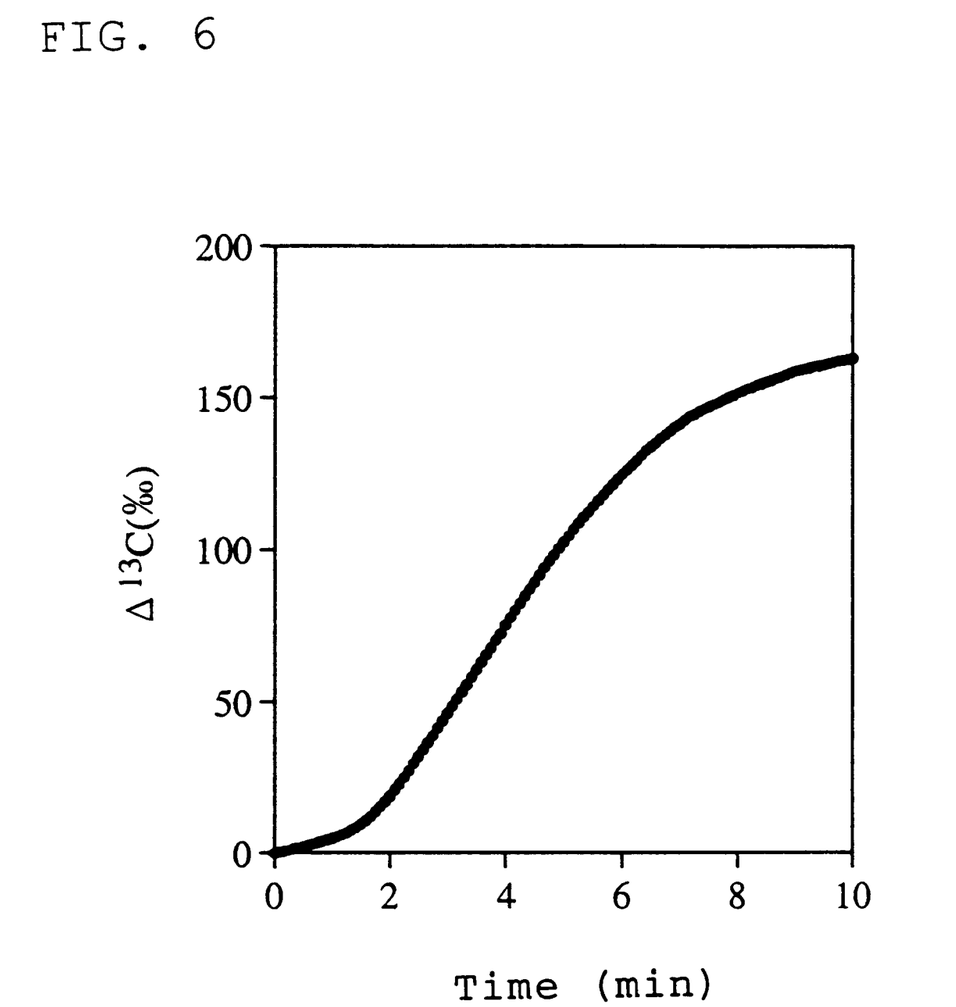
FIG. 6 shows the time course of $^{13}C$ levels in exhaled $CO_2$ ($\Delta^{13}C$ (‰)) after the administration of 1-$^{13}C$-methionine performed immediately before a partial liver excision (n=25).
Figure 7:
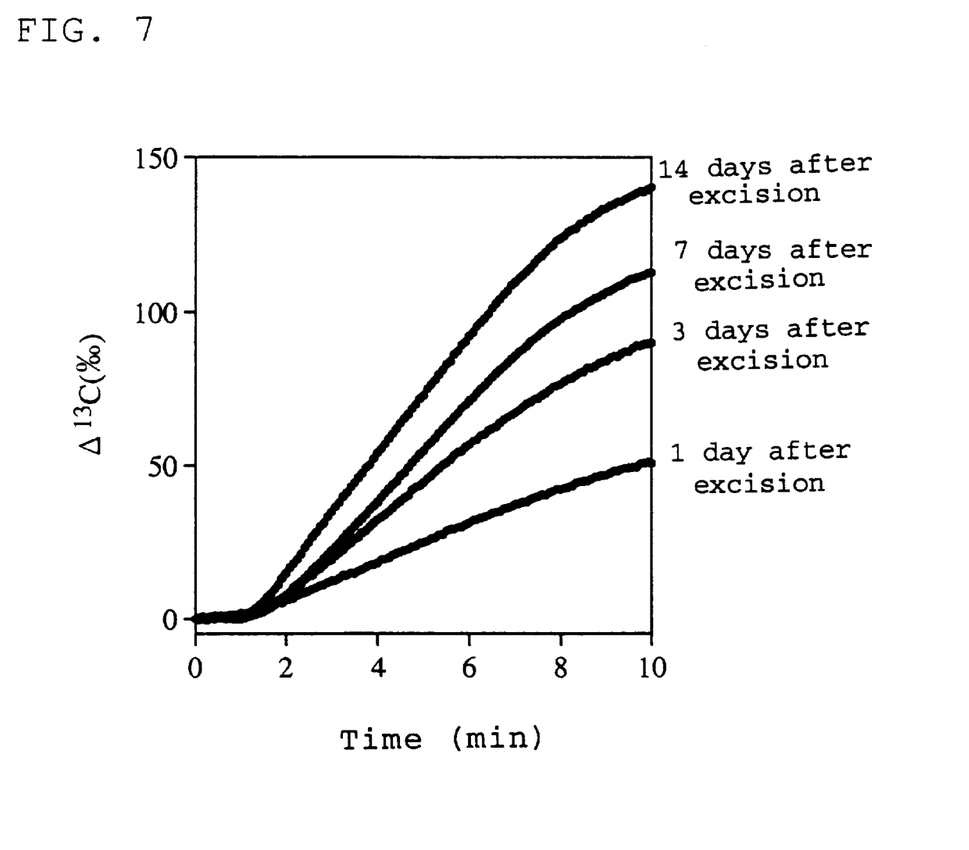
FIG. 7 shows the time course of $^{13}C$ levels in exhaled $CO_2$ ($\Delta^{13}C$ (‰)) after the administration of 1-$^{13}C$-methionine performed 1 day (n=6), 3 days (n=6), 7 days (n=7) or 14 days (n=6) after a partial liver excision.

In the measurement of $^{13}$C levels in exhaled $CO_2$ after intravenous administration of 1-$^{13}$C-methionine performed immediately before the the liver excision, the $\Delta^{13}$C value (‰) continued increasing for 10 min after the administration (FIG. 6). Ten minutes after the administration, the $\Delta^{13}$C value was 162.9±31.9 ‰ (n=25). After the partial liver excision, the $\Delta^{13}$C (‰) value exhibited the same pattern as seen before the excision in that the value continued increasing for 10 min after administration of 1-$^{13}$C-methionine. However, the $\Delta^{13}$C value at 10 min after the administration was remarkably decreased (50.7±11.1 ‰ (n=6)) at day 1 after the excision. This value increased to 89.9±3.8 ‰ (n=6) at day 3, to 112.7±21.7 ‰ (n=7) at day 3, and to 140.2±7.3 ‰ (n=7) at day 14 after the excision, as the liver regeneration progressed (FIG. 7).

Figure 8:
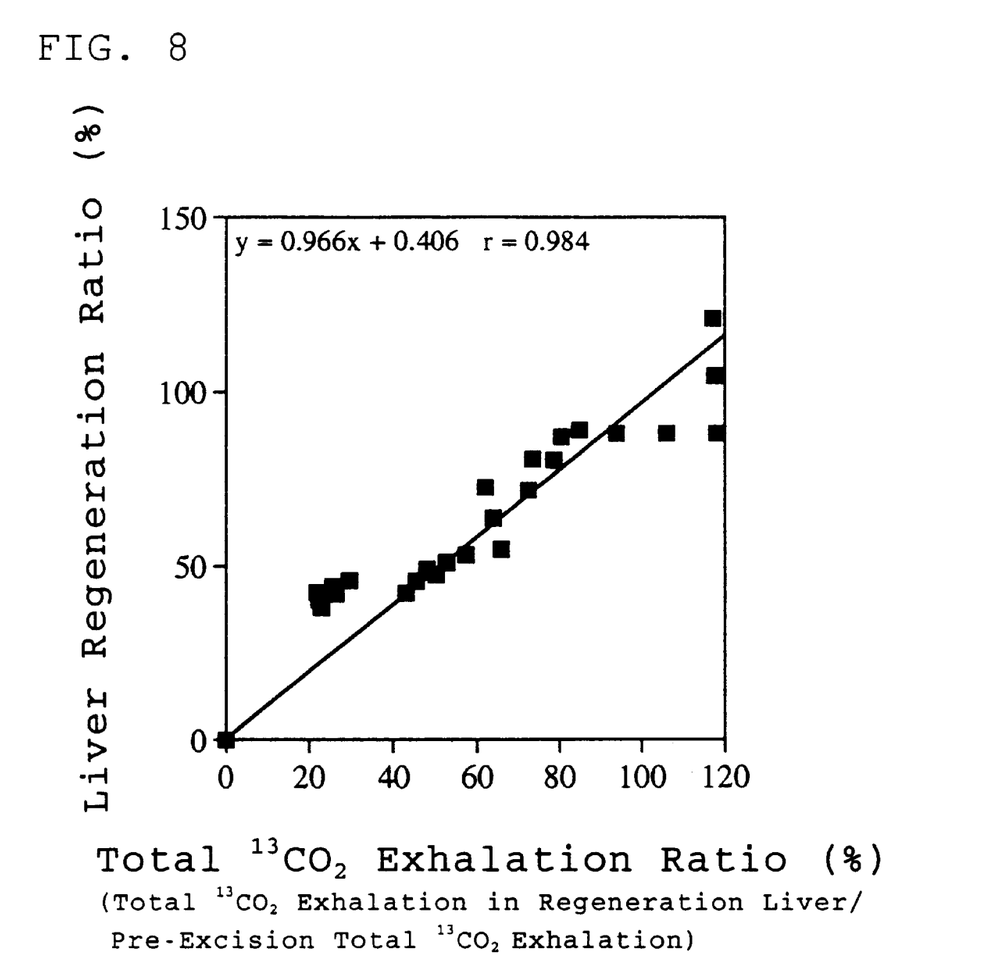
FIG. 8 shows correlation between individual liver excision ratios and ratios of the post-excision/breeding total amount of $^{13}CO_2$ exhalation for 10 min after administration of 1-$^{13}C$-methionine to the pre-excision total amount of $^{13}CO_2$ exhalation for 10 min after administration of 1-$^{13}C$-methionine, i.e. [post-excision/breeding total amount of $^{13}CO_2$ exhalation for the 10 min (A.U.)/pre-excision total amount of $^{13}CO_2$ exhalation for the 10 min (A.U.)]×100(%).

When individual liver regeneration ratios (%) and ratios of the post-excision/breeding total amount of $^{13}CO_2$ exhalation for 10 min after administration of 1-$^{13}$C-methionine to the pre-excision total amount of $^{13}CO_2$ exhalation for 10 min after administration of 1-$^{13}$C-methionine, i.e. [post-excision/breeding total amount of $^{13}CO_2$ exhalation for the 10 min (A.U.)/pre-excision total amount of $^{13}CO_2$ exhalation (A.U.) for the 10 min]×100(%) were plotted, high correlation (correlation factor: 0.939) was observed (FIG. 8).

Accordingly, by comparing the total amount of $^{13}CO_3$ exhalation for 10 min after administration of 1-$^{13}$C-methionine before the excision with that amount during the course of recovery after the excision, the liver regeneration ratio can be evaluated.

EXAMPLE 4

Measurement of Liver Weight (by 1-1$^{13}$C-methionine, 1-$^{13}$C-alanine, 1-$^{13}$C-galactose and 1-$^{13}$C-fructose breath tests)

I. Methods (1) Preparation of partially liver-excised rats

As test animals, male Wister rats were bred at 23±2° C. under 55±10% humidity before use. The rats (12–15 week-old) fasted overnight were anesthetized by intraperitoneal administration of Nembutal (50 mg/kg), and then the abdomen was opened. According to the method of Higgins and Anderson (Archives of Pathology 12, 183, 1931), the left lobe of the liver was excised in Group A; the middle and left lobes of the liver were excised in Group B; and the middle, left and right lobes of the liver were excised in Group C. Thus, 3 types of partially liver-excised rats were prepared.

(2) Measurement of $^{13}$C levels in exhaled $CO_2$

Measurement of $^{13}$C levels in exhaled $CO_2$ was performed in the rats 3 to 5 days before the partial liver excision and immediately after the excision as described below.

The rat anesthetized by intraperitoneal administration of Nembutal (50 mg/kg) was fixed on an operation table. The head was covered with a cap for sucking the exhalation, which was sucked with a stroke pump (variable stroke pump VS-500; Shibata Scientific Technology) at a rate of 100 ml/min and introduced into a flow cell in $^{13}CO_2$ Analyzer EX-130S (Japan Spectroscopic Co., Ltd.). After the $CO_2$ gas concentration in the sucked exhalation was stabilized at about 3%, 1-$^{13}$C-methionine (purchased from mass Trace) (40 mg/kg), 1-$^{13}$C-alanine (purchased from mass Trace) (20 mg/kg), 1-$^{13}$C-galactose (purchased from ICON) (100 mg/kg) or 1-$^{13}$C-fructose (purchased from ICON) (100 mg/kg) dissolved in physiological saline was administered from the femoral vein. A Perma Pure Drier (MD-050-12P, Perma Pure Inc.) was located between the cap and the stroke pump to remove the moisture in the exhalation. During the measurement of $^{13}$C levels in exhaled $CO_2$, the rectum temperature in the rat was monitored and maintained at 37±0.5° C. using a body temperature controller for small animals (TR-100; Fine Science Tools Inc.).

The data output from the $^{13}CO_2$ analyzer were incorporated into a personal computer (Apple Power Macintosh 8500) after AD conversion. Using the data processing software Lab VIEW (National Instruments), data on 10 points at every 100 msec were added up and averaged at intervals of 5 sec and then converted into $^{13}$C atom %, $\Delta^{13}$C (‰) and $CO_2$ gas concentration (%), to thereby perform a continuous measurement. The converted data were displayed on the screen in real time and then stored in the hard disk. $\Delta^{13}C$ (‰) was calculated by the formula described previously.

(3) Measurement of the liver weight

After completion of the measurement of $^{13}C$ levels in exhaled $CO_2$ performed after the partial liver excision, the remaining liver was removed and immediately weighed to obtain the liver weight after the excision (i.e., weight of the remaining liver). Also, the total weight of the excised portion and the remaining liver was taken as the liver weight before the excision.

II. Results (1) 1-$^{13}C$-methionine breath test

Figure 9:
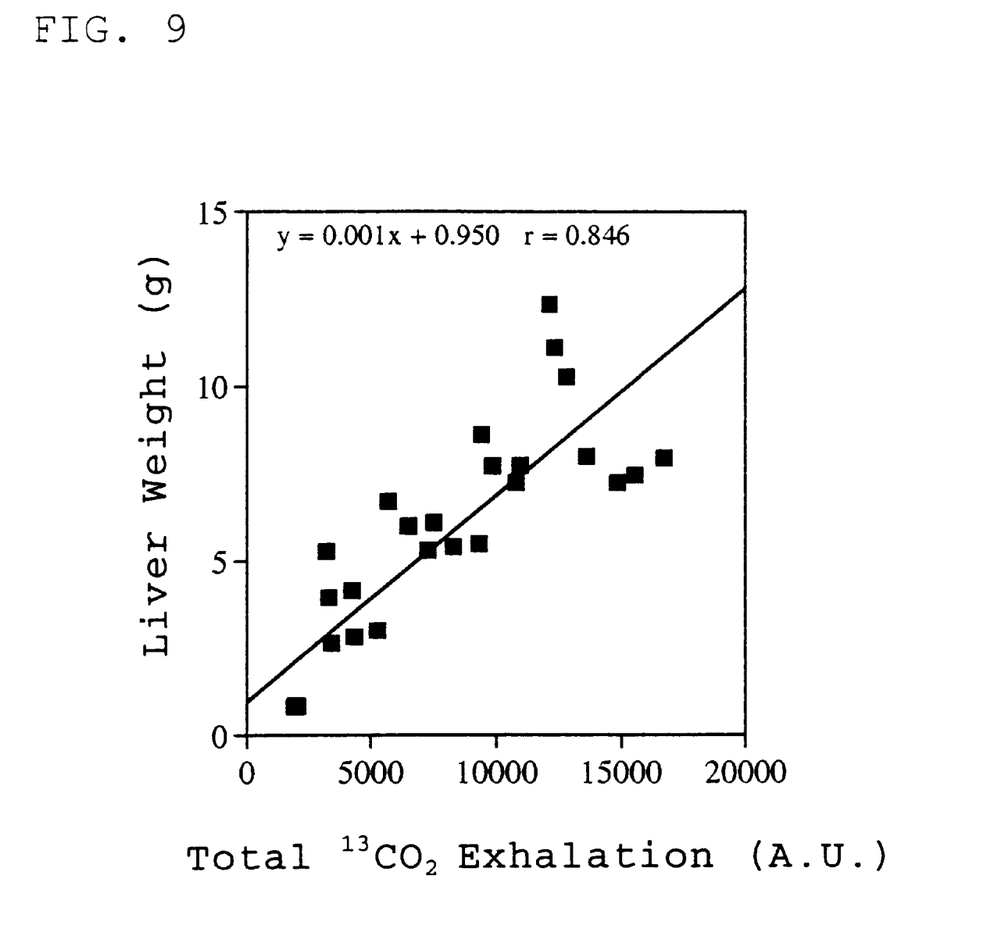
FIG. 9 shows correlation between individual liver weights and the total amounts of $^{13}CO_2$ exhalation for 10 min after administration of 1-$^{13}C$-methionine.

When individual liver weights (g) after the excision and total amounts of $^{13}CO_2$ exhalation for 10 min after administration of 1-$^{13}C$-methionine ($^{13}C$ levels in exhaled $CO_2$ for 10 min from the administration added up) were plotted, correlation was observed with a correlation factor of 0.846 (FIG. 9).

Therefore, it is possible to evaluate the liver weight after the excision from the total amount of $^{13}CO_2$ exhalation for 10 min after administration of 1-$^{13}C$-methionine.

(2) 1-$^{13}C$-alanine breath test

Figure 10:
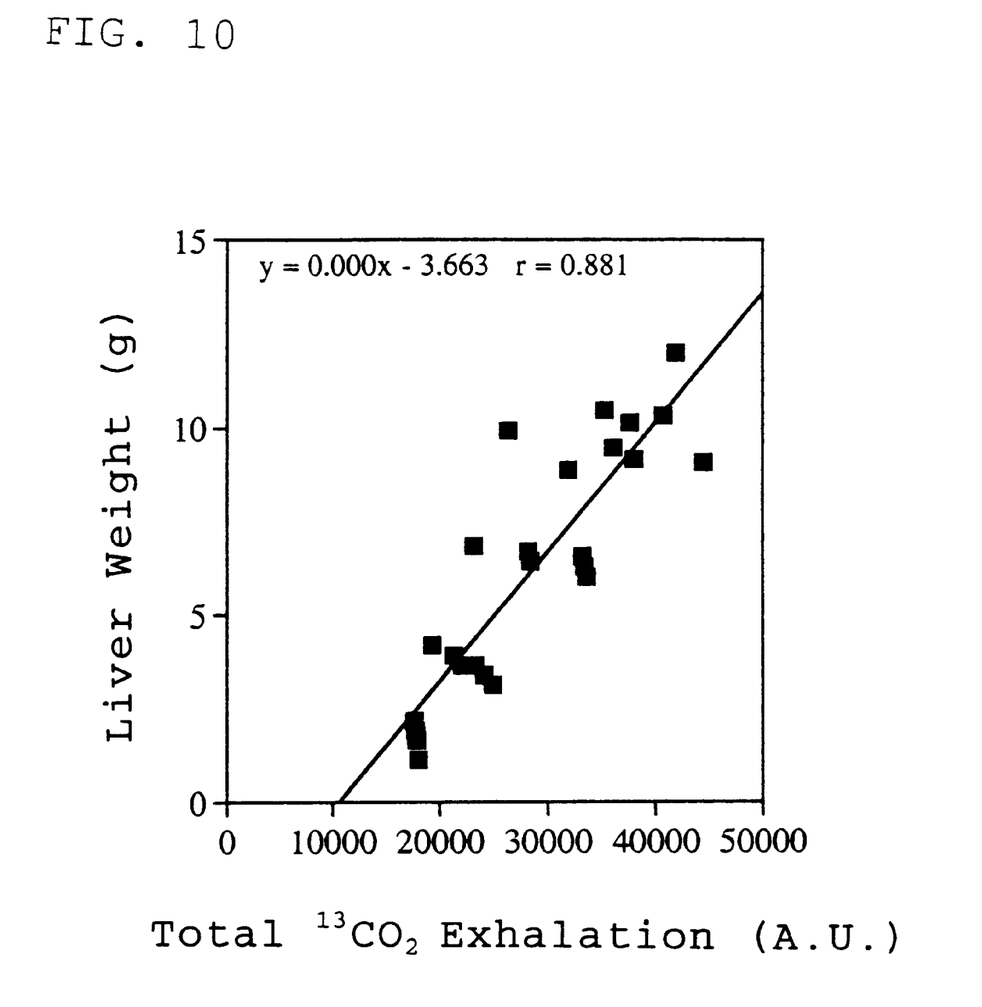
FIG. 10 shows correlation between individual liver weights and the total amounts of $^{13}CO_2$ exhalation for 10 min after administration of 1-$^{13}C$-alanine.

When individual liver weights (g) after the excision and total amounts of $^{13}CO_2$ exhalation for 10 min after administration of 1-$^{13}C$-alanine ($^{13}C$ levels in exhaled $CO_2$ for 10 min from the administration added up) were plotted, correlation was observed with a correlation factor of 0.881 (FIG. 10).

Therefore, it is possible to evaluate the liver weight after the excision from the total amount of $^{13}CO_2$ exhalation for 10 min after administration of 1-$^{13}C$-alanine.

(3) 1-$^{13}C$-fructose breath test

Figure 11:
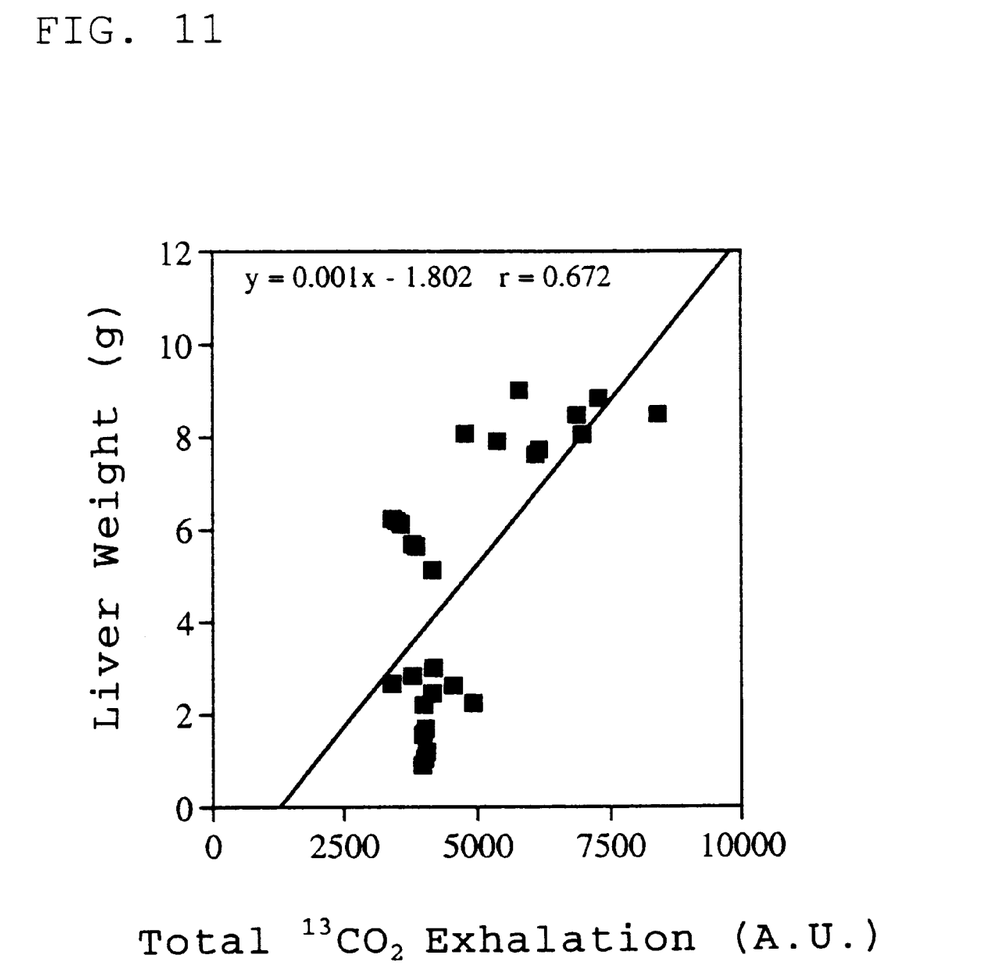
FIG. 11 shows correlation between individual liver weights and the total amounts of $^{13}CO_2$ exhalation for 10 min after administration of 1-$^{13}C$-fructose.

When individual liver weights (g) after the excision and total amounts of $^{13}CO_2$ exhalation for 10 min after administration of 1-$^{13}C$-fructose ($^{13}C$ levels in exhaled $CO_2$ for 10 min from the administration added up) were plotted, correlation was observed with a correlation factor of 0.672 (FIG. 11).

Therefore, it is possible to evaluate the liver weight after the excision from the total amount of $^{13}CO_2$ exhalation for 10 min after administration of 1-$^{13}$-C-fructose.

(4) 1-$^{13}C$-galactose breath test

Figure 12:
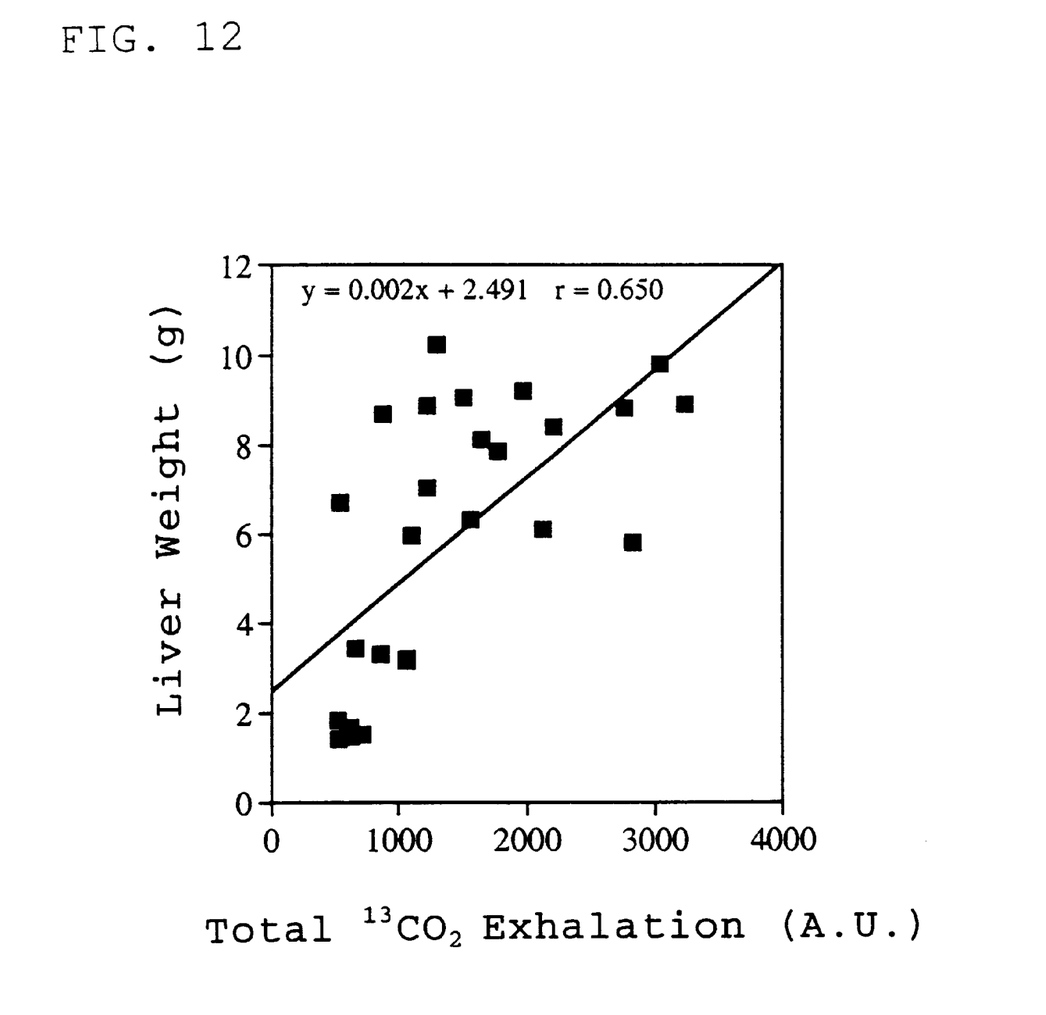
FIG. 12 shows correlation between individual liver weights and the total amounts of $^{13}CO_2$ exhalation for 10 min after administration of 1-$^{13}C$-galactose.

When individual liver weights (g) after the excision and total amounts of $^{13}CO_2$ exhalation for 10 min after administration of 1-$^{13}C$-galactose ($^{13}C$ levels in exhaled $CO_2$ for 10 min from the administration added up) were plotted, correlation was observed with a correlation factor of 0.650 (FIG. 12).

Therefore, it is possible to evaluate the liver weight after the excision from the total amount of $^{13}CO_2$ exhalation for 10 min after administration of 1-$^{13}C$-galactose.

Formulation Example 1

(Injection)

10 parts by weight of 1-$^{13}C$-phenylalanine was dissolved in 90 parts by weight of physiological saline and sterilized by filtration with a Millipore filter. The filtrate was put into a vial and sealed to give an injection.

Formulation Example 2

(Internal Liquid Agent)

10 parts by weight of 1-$^{13}C$-phenylalanine was dissolved in 90 parts by weight of DDW and sterilized by filtration with a Millipore filter. The filtrate was put into a vial and sealed to give an internal liquid agent.

Formulation Example 3

(Injection)

10 parts by weight of 1-$^{13}C$-methionine was dissolved in 90 parts by weight of physiological saline and sterilized by filtration with a Millipore filter. The filtrate was put into a vial and sealed to give an injection.

Formulation Example 4

(Injection)

10 parts by weight of 1-$^{13}C$-fructose was dissolved in 90 parts by weight of physiological saline and sterilized by filtration with a Millipore filter. The filtrate was put into a vial and sealed to give an injection.

What is claimed is:

1. A method of evaluating hepatic operation, comprising (1) administering to a subject an aromatic amino acid, methionine, alanine, fructose or galactose labeled with $^{13}C$ at least at one position before a hepatic operation; (2) measuring $^{13}C$ levels in the exhaled $CO_2$ after the administration; (3) administering to a subject an aromatic amino acid, methionine, alanine, fructose or galactose labeled with $^{13}C$ at least at one position after the hepatic operation; (4) measuring 13C levels in the exhaled $CO_2$ after the administration; and (5) comparing the degrees of increase of the $^{13}C$ levels measured before and after the hepatic operation.

2. The method according to claim 1, wherein the aromatic amino acid is phenylalanine or tyrosine.

3. A method for evaluating a hepatic operation, comprising (1) administering to a subject phenylalanine, tyrosine, methionine, alanine, fructose, or galactose labeled with $^{13}C$ at position 1 before a hepatic operation; (2) measuring $^{13}C$ levels in exhaled $CO_2$ after the administration; (3) administering to a subject phenylalanine, tyrosine, methionine, alanine, fructose, or galactose labeled with 13C at position 1 after the hepatic operation; (4) measuring $^{13}C$ levels in the exhaled $CO_2$ after the administration; and (5) comparing the degrees of increase of the $^{13}C$ levels measured before and after the hepatic operation.

4. The method according to claim 1, wherein the evaluation of the hepatic operation is carried out by measuring the liver excision ratio of a subject after the hepatic operation.

5. The method according to claim 1, wherein the evaluation of the hepatic operation is carried out by measuring the liver regeneration/increase ratio of a subject after the operation.

6. The method according to claim 1, wherein the evaluation of the hepatic operation is carried out by measuring the liver weight of a subject after the operation.

7. The method according to claim 3, wherein the evaluation of the hepatic operation is carried out by measuring the liver excision ratio of a subject after the hepatic operation.

8. The method according to claim 3, wherein the evaluation of the hepatic operation is carried out by measuring the liver regeneration/increase ratio of a subject after the operation.

9. The method according to claim 3, wherein the evaluation of the hepatic operation is carried out by measuring the liver weight of a subject after the operation.

* * * * *